United States Patent
Trahan

(10) Patent No.: US 9,198,745 B1
(45) Date of Patent: Dec. 1, 2015

(54) ORAL APPLIANCE CLEANER AND HOLDER

(71) Applicant: Christopher J. Trahan, Lake Charles, LA (US)

(72) Inventor: Christopher J. Trahan, Lake Charles, LA (US)

( * ) Notice: Subject to any disclaimer, the term of this patent is extended or adjusted under 35 U.S.C. 154(b) by 0 days.

(21) Appl. No.: 14/709,244

(22) Filed: May 11, 2015

Related U.S. Application Data

(60) Provisional application No. 62/048,913, filed on Sep. 11, 2014.

(51) Int. Cl.
*A46B 7/08* (2006.01)
*A61C 17/00* (2006.01)
*A46B 5/00* (2006.01)
*B08B 1/00* (2006.01)
*B08B 3/04* (2006.01)

(52) U.S. Cl.
CPC ............. *A61C 17/036* (2013.01); *A46B 5/0004* (2013.01); *A46B 7/08* (2013.01); *B08B 1/002* (2013.01); *B08B 3/04* (2013.01)

(58) Field of Classification Search
CPC ........ A61C 17/036; A46B 5/0004; A46B 7/08
See application file for complete search history.

(56) References Cited

U.S. PATENT DOCUMENTS

| | | | | |
|---|---|---|---|---|
| 3,774,256 | A | * 11/1973 | Gauthier | ................. 15/21.1 |
| 5,298,077 | A | * 3/1994 | Saarela et al. | ................. 134/6 |
| 6,079,075 | A | * 6/2000 | Velez-Juan | ................. 15/167.1 |

* cited by examiner

*Primary Examiner* — Shay Karls

(57) ABSTRACT

An oral appliance cleaner and holder is a device that is used to clean an oral appliance via scrubbing in conjunction with a liquid cleaning solution. The oral appliance is placed in between a first brush and a second brush. The first brush is able to rotate along with a rotatable base in order to scrub the oral appliance. The rotatable base is mounted to a fluid reservoir that transfers liquid cleaning solution to the first brush and the second brush. A lid and a sealing ring are used to prevent leakage of the liquid cleaning solution from the fluid reservoir. A plurality of slots is present in the first brush and the second brush to allow the liquid cleaning solution to pass from the fluid reservoir and come into contact with a plurality of bristles of the first brush and a plurality of bristles of the second brush.

14 Claims, 8 Drawing Sheets

SECTION A-A

SECTION B-B

SECTION C-C

ORAL APPLIANCE CLEANER AND HOLDER

The current application claims a priority to the U.S. Provisional Patent application Ser. No. 62/048,913 filed on Sep. 11, 2014.

FIELD OF THE INVENTION

The present invention relates generally to a device for oral appliance hygiene and maintenance. More specifically, the present invention is an oral appliance cleaner and holder that is utilized to thoroughly clean the surfaces of an oral appliance in conjunction with a liquid cleaning solution.

BACKGROUND OF THE INVENTION

Oral appliances are utilized for a wide variety of dental purposes and are available in many forms. Mandibular advancement devices (MAD) and tongue retaining devices are commonly worn to promote airflow in cases of sleep apnea. Retainers are worn during the retention phase immediately following the removal of orthodontic braces. Dentures are often worn by those who have lost teeth to disease, decay, injury, or other causes. Finally, another common oral appliance is the mouth guard. Mouth guards are worn by athletes to protect their teeth in contact sports as well as those who are suffering from bruxism (excessive grinding of the teeth). Because these oral appliances are often worn for long periods of time (such as when sleeping) and due to the presence of large amounts of bacteria in the mouth, it is necessary to frequently clean the oral appliances after use. Bacteria and other contaminants may accumulate and form a biofilm on the surfaces of oral appliances, similar to dental plaque. One of the most common means of cleaning and oral appliance is by submerging the oral appliance in warm water with a denture cleaner (often in tablet form) in order to kill harmful bacteria on the oral appliance. However, in order to most thoroughly clean the oral appliance, it is often necessary to scrub the oral appliance with a brush or similar tool in addition to soaking the oral appliance in a cleaning solution. The present invention seeks to improve upon conventional means of cleaning oral appliances as well as provide the user with a convenient and straightforward means of maintaining the hygiene of oral appliances.

The present invention is an oral appliance cleaner and holder that allows the user to quickly and thoroughly clean an oral appliance. The present invention is utilized in conjunction with a liquid cleaning solution in order to both disinfect and scrub the oral appliance. The liquid cleaning solution is sealed within the present invention during the cleaning process. The present invention utilizes a rotating brush mechanism to allow the user to manually scrub the surface of the oral appliance.

DETAIL DESCRIPTIONS OF THE INVENTION

Figure 1:
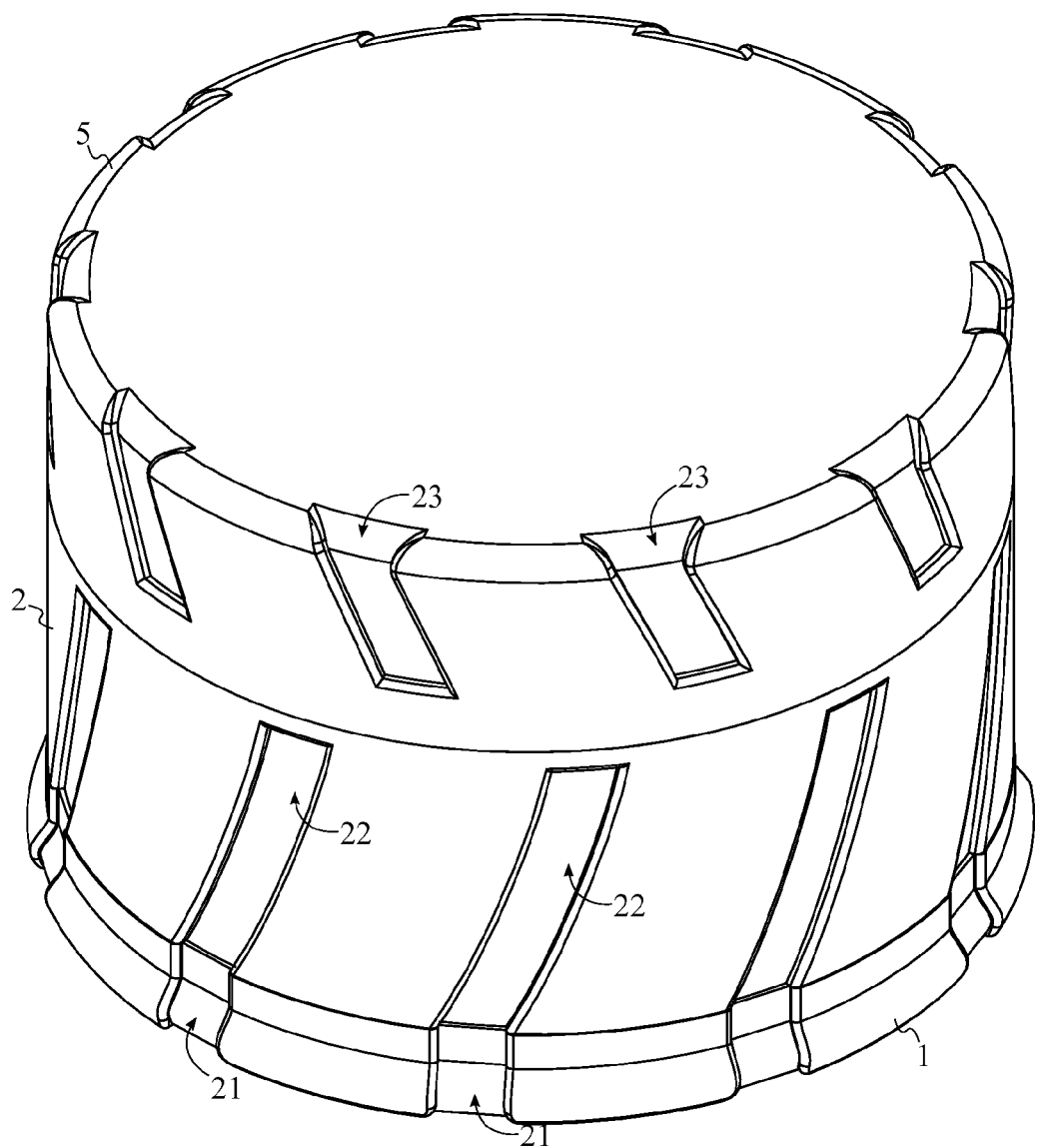
FIG. 1 is a perspective view of the present invention.
Figure 2:
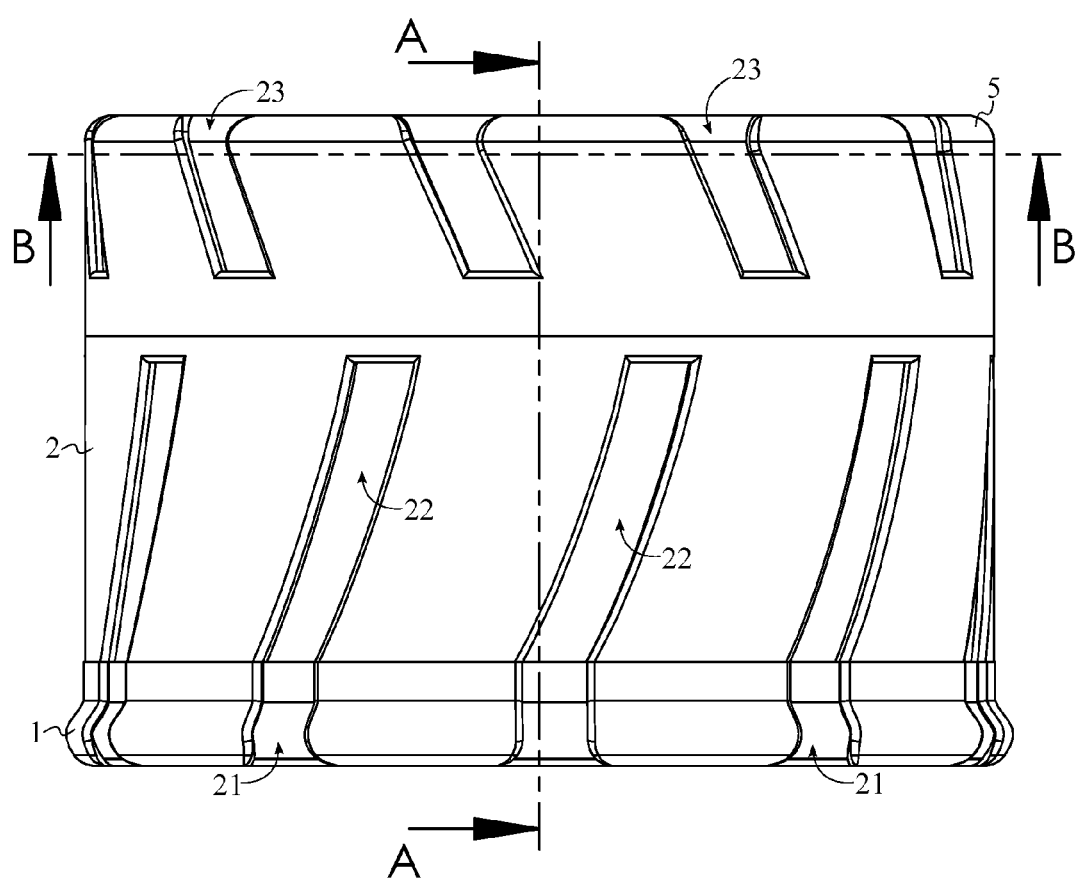
FIG. 2 is a front view of the present invention.

All illustrations of the drawings are for the purpose of describing selected versions of the present invention and are not intended to limit the scope of the present invention.

The present invention is an oral appliance cleaner and holder that is utilized to clean an oral appliance in conjunction with a liquid cleaning solution. The present invention is shown in FIGS. 1-8 and comprises a rotatable base 1, a fluid reservoir 2, a lid 5, a first brush 7, and a second brush 8.

The rotatable base 1 is physically grasped by the user and rotated during cleaning of the oral appliance. Rotational motion is transferred to the first brush 7 by the rotatable base 1, and the rotational motion allows the first brush 7 to scrub the oral appliance. The rotatable base 1 is rotatably mounted into the fluid reservoir 2 in order to allow the user to externally grasp the fluid reservoir 2 while allowing the rotatable base 2 to freely move within the fluid reservoir 2. The first brush 7 and the second brush 8 each comprise a base plate 9 and a plurality of bristles 10 for scrubbing the oral appliance. As shown in FIG. 3 and FIGS. 5-8, the plurality of bristles 10 for the first brush 7 and the plurality of bristles 10 for the second brush 8 are oriented towards each other in order to allow the oral appliance to be placed in between the plurality of bristles 10 for the first brush 7 and the plurality of bristles 10 for the second brush 8. The base plate 9 of the first brush 7 is removably and axially mounted to the rotatable base 1. As such, when the rotatable base 1 is rotated, rotational motion is transferred to the first brush 7, allowing the first brush 7 to scrub the oral appliance. Additionally, this allows the first brush 7 to be removed from the rotatable base 1 for cleaning or replacement. The fluid reservoir 2 holds a quantity of liquid cleaning solution and comprises a reservoir open end 3 through which the fluid reservoir 2 may be emptied or filled. The liquid cleaning solution is transferred to the plurality of bristles 10 of the first brush 7 and the second brush 8 during cleaning. The lid 5 ensures that the liquid cleaning solution cannot leak from the present invention and additionally serves as a base for the second brush 8. The lid 5 comprises a lid open end 6 that allows the second brush 8 to be mounted within the lid 5. The second brush 8 provides additional scrubbing for the side of the oral appliance opposite to the side undergoing scrubbing by the first brush 7.

The present invention may be assembled as shown in FIGS. 5-8. The base plate 9 of the first brush 7 is positioned in between the fluid reservoir 2 and the reservoir open end 3. This allows the liquid cleaning solution to be transferred from the fluid reservoir 2 and through the base plate 9 of the first brush 7 plate in order to come into contact with the plurality of bristles 10 of the first brush 7 and the second brush 8. The fluid reservoir 2 is in fluid communication with the lid 5 through the base plate 9 of the first brush 7 and through the base plate 9 of the second brush 8. As such, the first brush 7 and the second brush 8 may be used interchangeably without compromising the ability of the liquid cleaning solution to pass through the first brush 7 or the second brush 8. The lid 5 is removably attached into the fluid reservoir 2, opposite the rotatable base 1. This allows the oral appliance to be placed in between the first brush 7 and the second brush 8 and additionally allows the lid 5 to seal the fluid reservoir 2, preventing liquid cleaning solution from escaping. The base plate 9 of the second brush 8 is removably mounted into the lid 5, allowing the second brush 8 to be secured into the lid 5 and positioning the second brush 8 opposite to the first brush 7. Additionally, the base plate 9 of the second brush 8 is positioned offset and concentric with the base plate 9 of the first brush 7. This ensures that the second brush 8 remains in alignment with the first brush 7 during the cleaning process.

Figure 3:
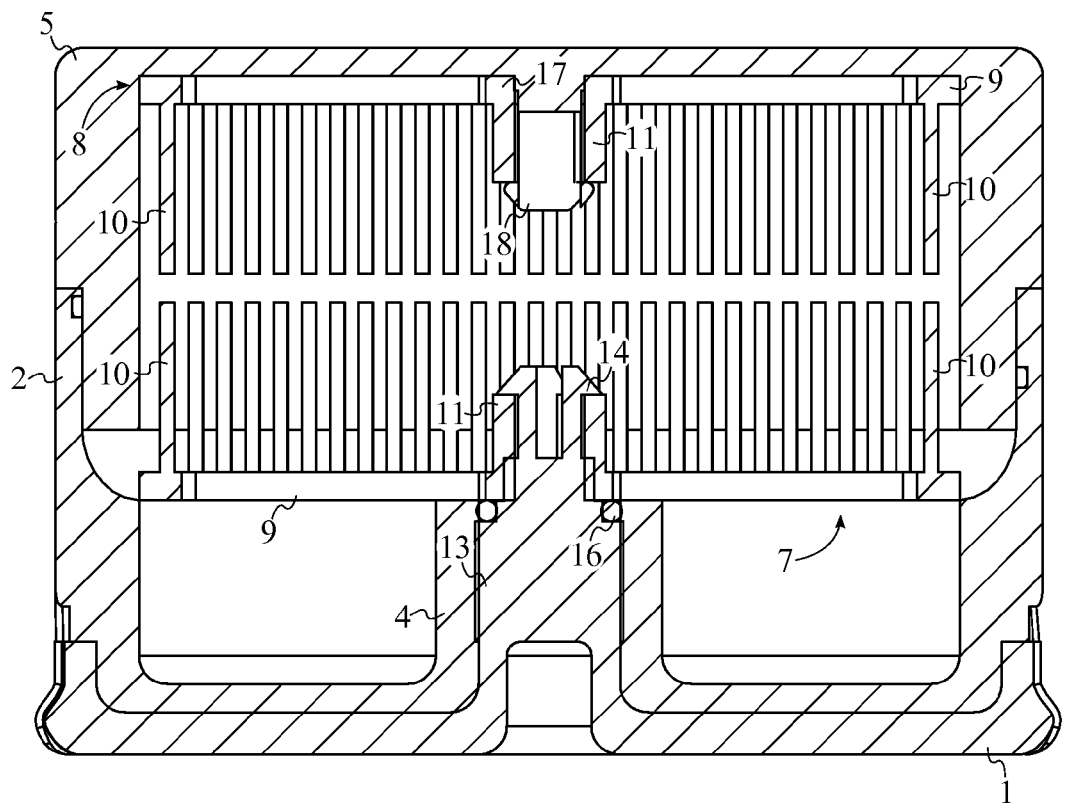
FIG. 3 is a cross-sectional view of the present invention taken along line A-A of FIG. 2.
Figure 5:
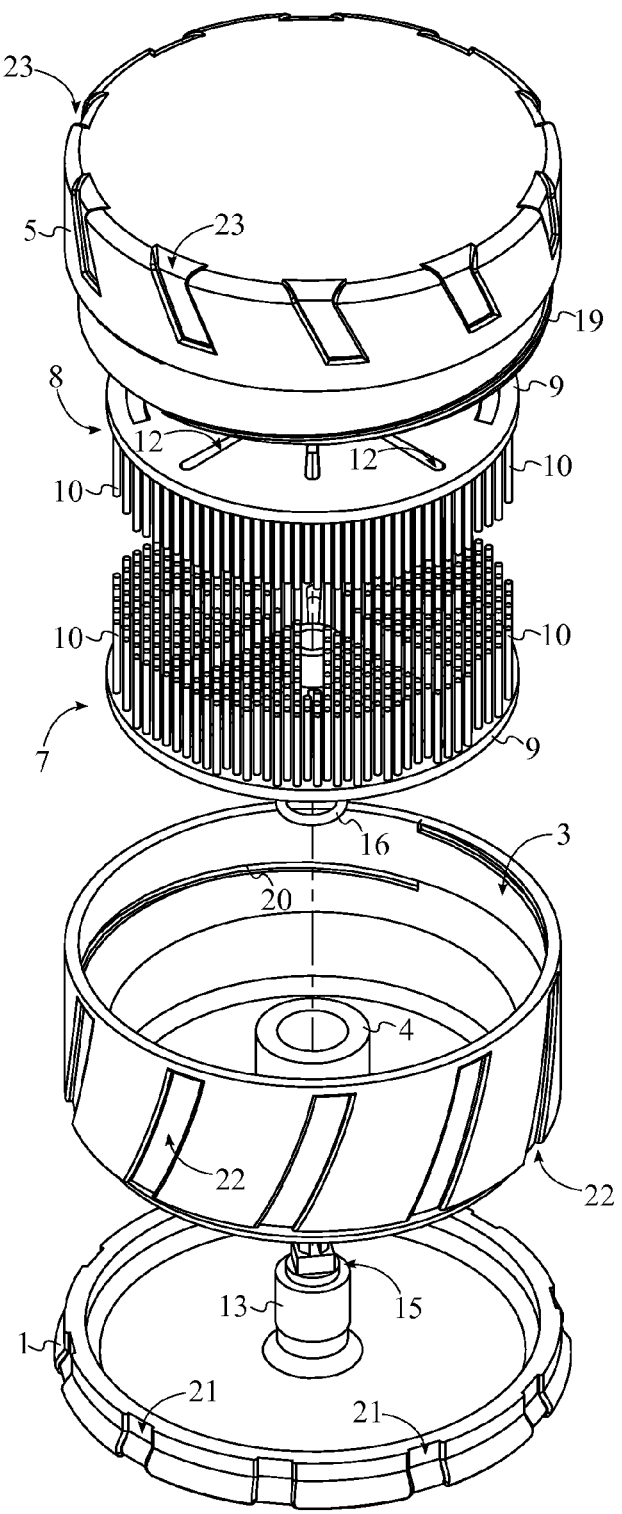
FIG. 5 is an exploded top-perspective view of the present invention.
Figure 6:
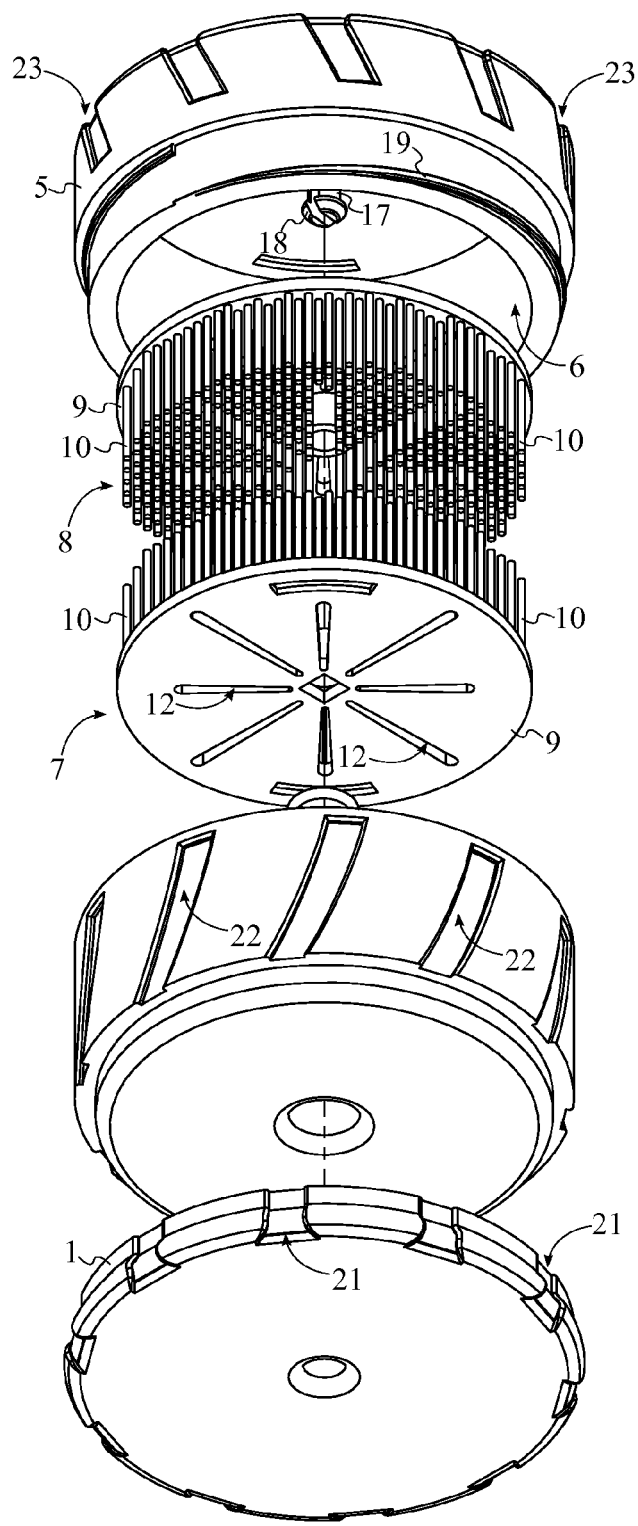
FIG. 6 is an exploded bottom-perspective view of the present invention.
Figure 7:
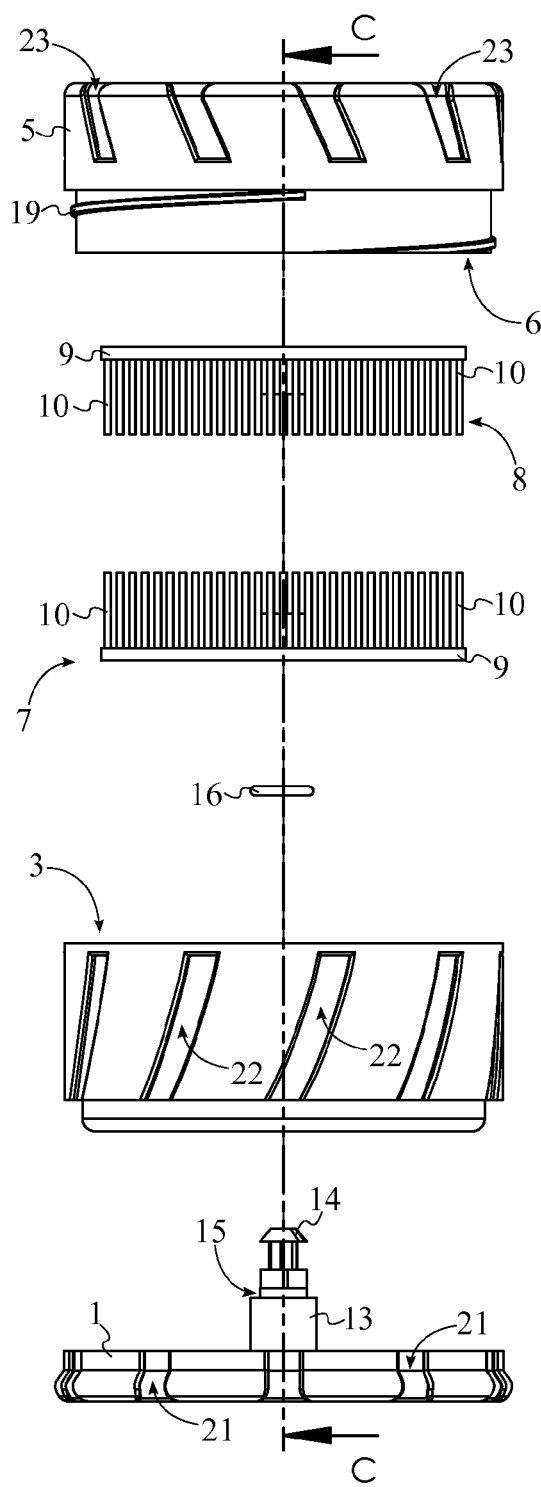
FIG. 7 is an exploded front view of the present invention.
Figure 8:
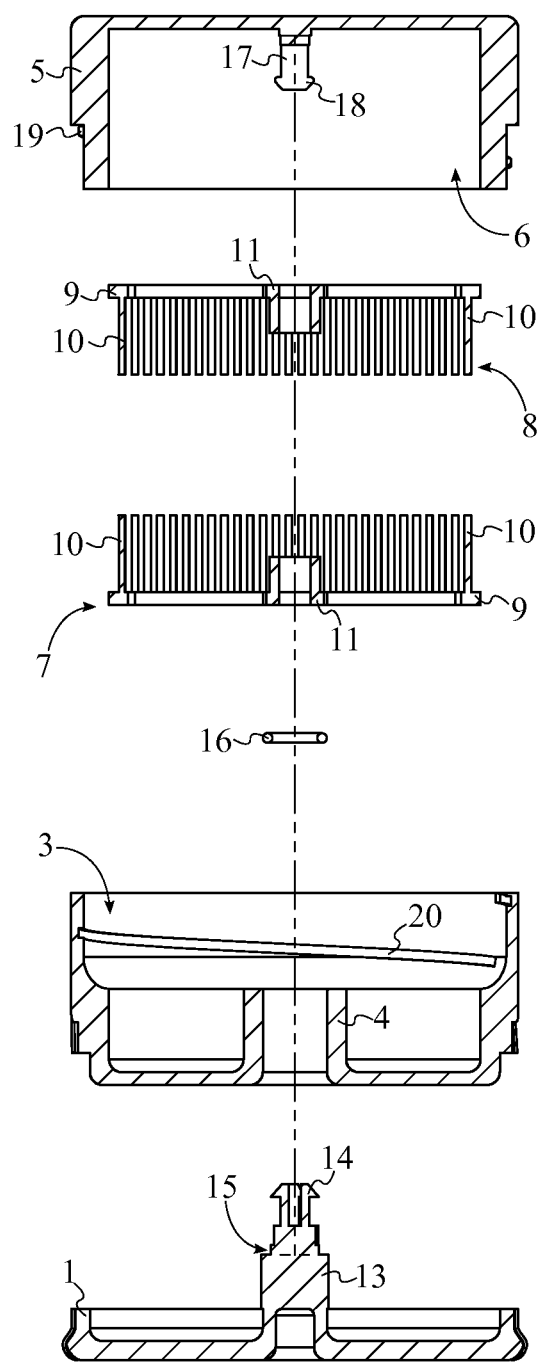
FIG. 8 is a cross-sectional view of the present invention taken along line C-C of FIG. 7.

The present invention further comprises a first stem 13. The first stem 13 is utilized to mount the first brush 7 as well as to secure the fluid reservoir 2 to the rotatable base 1. As shown in FIG. 3, FIG. 5, and FIG. 8, the fluid reservoir 2 further comprises a reservoir collar 4 that assists in securing the fluid reservoir 2 to the rotatable base 1 along with the first stem 13. The first brush 7 further comprises a plate collar 11 that serves to secure the first brush 7 to the rotatable base 1, allowing the first brush 7 to rotate along with the rotatable base 1. The first stem 13 is connected normal to the rotatable base 1, allowing the first stem 13 to protrude from the rotatable base 1 and allowing the fluid reservoir 2 and the first brush 7 to be mounted to the rotatable base 1. The first stem 13 is positioned centrally to the base plate 9 of the first brush 7. This allows the first brush 7 to be mounted to the first stem 13, secured to the rotatable base 1, and rotated along with the rotatable base 1. The first stem 13 is rotatably mounted through the reservoir collar 4, allowing the rotatable base 1 to be secured to the fluid reservoir 2 without causing the fluid reservoir 2 to rotate along with the rotatable base 1. As shown in FIG. 3, the first stem 13 is axially attached to the plate collar 11 of the first brush 7, causing the first brush 7 to rotate along with the rotatable base 1 while allowing the first brush 7 to be separated from the rotatable base 1 as needed.

Again with reference to FIG. 3 and FIGS. 5-8, the present invention further comprises a first squeeze lock 14, an annular receiving cavity 15, and a sealing ring 16. The first squeeze lock 14 is utilized to lock the first brush 7 to the first stem 13 and prevent the first brush 7 from separating from the first stem 13 during use of the present invention. The sealing ring 16 prevents liquid cleaning solution from leaking out of the fluid reservoir 2 as shown in FIG. 3. The annular receiving cavity 15 is utilized to retain the sealing ring 16. The first stem 13 is axially attached to the plate collar 11 of the first brush 7 by the first squeeze lock 14. As such, the first squeeze lock 14 is able to retain the first brush 7 by securing the plate collar 11 of the first brush 7 and the base plate 9 of the first brush 7 in between the first squeeze lock 14 and the reservoir collar 4. The annular receiving cavity 15 is integrated around the first stem 13, adjacent to the base plate 9 of the first brush 7. Additionally, the annular receiving cavity 15 is engaged by the sealing ring 16. This ensures that the sealing ring 16 may be installed around the first stem 13, preventing liquid cleaning solution from escaping the fluid reservoir 2.

The present invention further comprises a second stem 17. The second stem 17 is utilized to mount the second brush 8 to the lid 5. The second brush 8 further comprises a plate collar 11 that allows the second brush 8 to be secured to the lid 5. The second stem 17 is connected normal to the lid 5, allowing the second stem 17 to protrude from the lid 5 and hold the second brush 8 in place within the lid 5. The second stem 17 is positioned centrally to the base plate 9 of the second brush 8, placing the second stem 17 into alignment with the plate collar 11 of the second brush 8. The second stem 17 is axially attached to the plate collar 11 of the second brush 8 and the second brush 8 is secured to the lid 5 through the second stem 17.

The present invention further comprises a second squeeze lock 18. The second squeeze lock 18 functions in an identical manner as the first squeeze lock 14. The second squeeze lock 18 is utilized to lock the second brush 8 to the second stem 17 and prevents the second brush 8 from separating from the second stem 17. As shown in FIG. 3, the second stem 17 is axially attached to the plate collar 11 of the second brush 8 by the second squeeze lock 18. As such, the second squeeze lock 18 retains the second brush 8 in place and ensures that the second brush 8 does not separate from the second stem 17.

Figure 4:
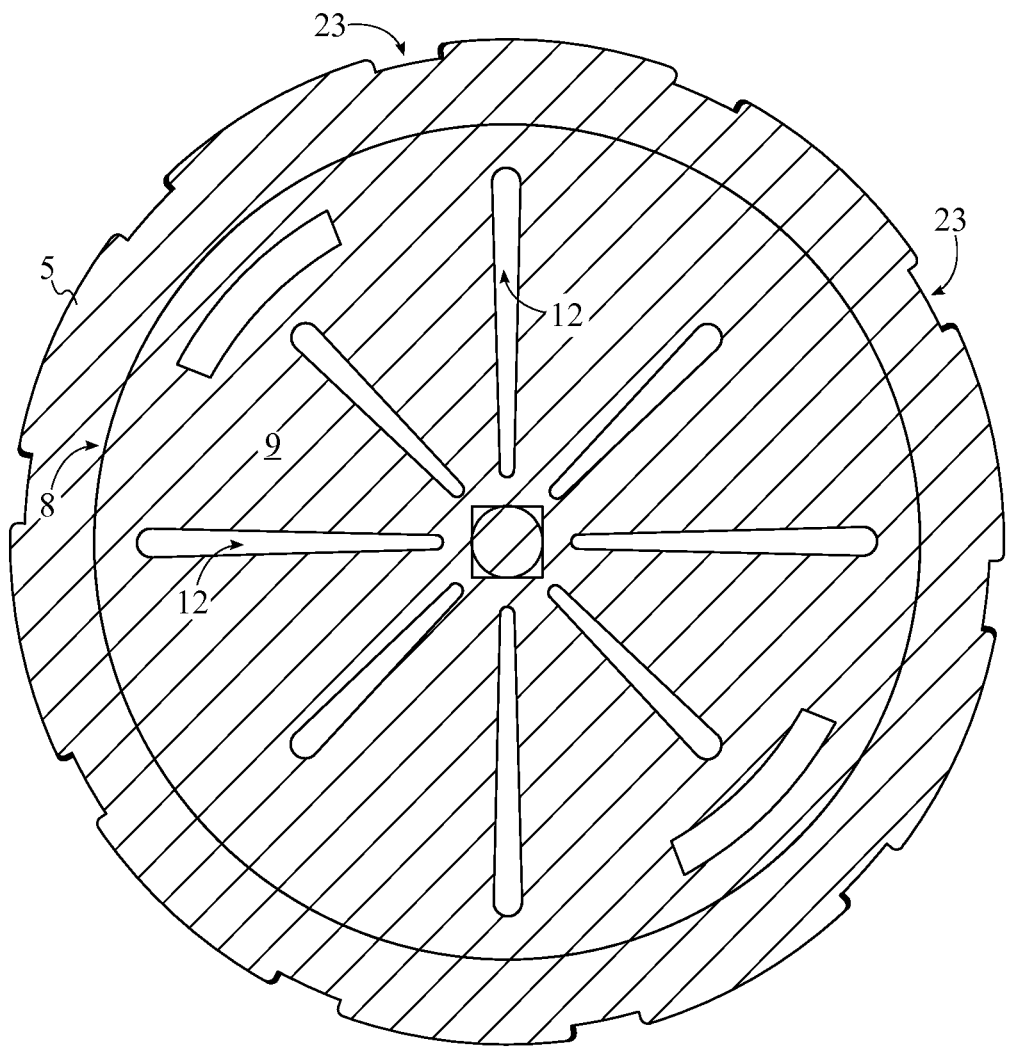
FIG. 4 is a cross-sectional view of the present invention taken along line B-B of FIG. 2.

The first brush 7 and the second brush 8 each further comprise a plurality of slots 12. The plurality of slots 12 allow liquid cleaning solution to pass through the first brush 7 and the second brush 8 and come into contact with the plurality of bristles 10 of the first brush 7 and the second brush 8. The plurality of slots 12 is present on both the first brush 7 and the second brush 8 in order to allow the first brush 7 and the second brush 8 to be utilized interchangeably. The plurality of slots 12 traverses through the base plate 9 of the first brush 7 and the base plate 9 of the second brush 8 and as such, the liquid cleaning solution is able to pass through the first brush 7 and the second brush 8. The plurality of slots 12 is radially distributed about the base plate 9 of the first brush 7 and the base plate 9 of the second brush 8 as shown in FIG. 4. This allows the liquid cleaning solution to evenly pass through the base plate 9 of the first brush 7 and the base plate 9 of the second brush 8. Once the oral appliance is in place in between the plurality of bristles 10 of the first brush 7 and the plurality of bristles 10 of the second brush 8, the present invention may be flipped upside down in order to allow liquid cleaning solution within the fluid reservoir 2 to pass through the plurality of slots 12 of the first brush 7.

Again with reference to FIGS. 5-8, the present invention further comprises a male threading 19 and a female threading 20 that allow the lid 5 to be secured to the fluid reservoir 2 and prevent liquid cleaning solution from escaping the fluid reservoir 2 along with the sealing ring 16. The male threading 19 is helically connected around the lid 5, adjacent to the lid open end 6. The user may screw the lid 5 onto the fluid reservoir 2 and secure the lid 5 in place to prevent leakage from within the fluid reservoir 2 and the lid 5. The female threading 20 is helically connected within the fluid reservoir 2, adjacent to the reservoir open end 3. This allows the lid 5 to be screwed into and held in place within the fluid reservoir 2. The male threading 19 is removably engaged to the female threading 20 to join the lid 5 and the fluid reservoir 2 together while allowing the user to easily separate the lid 5 from the fluid reservoir 2 as needed.

As shown in FIG. 1, FIG. 2, and FIGS. 5-7, the present invention further comprises a base grip 21, a reservoir grip 22, and a lid grip 23. The reservoir grip 22 and the lid grip 23 provide additional leverage to the user when grasping the fluid reservoir 2 and the lid 5, respectively. This allows the user to gain greater leverage on the fluid reservoir 2 and the lid 5 when attaching or removing the lid 5 from the fluid reservoir 2. The base grip 21 provides additional leverage for the user on the rotatable base 1 when rotating the rotatable base 1 in order to clean the oral appliance within the present invention. The base grip 21 is laterally integrated around the rotatable base 1, the reservoir grip 22 is laterally integrated around the fluid reservoir 2, and the lid grip 23 is laterally integrated around the lid 5. This allows the base grip 21, the reservoir grip 22, and the lid grip 23 to be circumferentially positioned around the rotatable base 1, the fluid reservoir 2, and the lid 5, respectively.

Although the present invention has been explained in relation to its preferred embodiment, it is understood that many other possible modifications and variations can be made without departing from the spirit and scope of the present invention as hereinafter claimed.

What is claimed is:
1. An oral appliance cleaner and holder comprises:
   a rotatable base;

a fluid reservoir;
a lid;
a first brush;
a second brush;
the fluid reservoir comprises a reservoir open end;
the lid comprises a lid open end;
the first brush and the second brush each comprise a base plate and a plurality of bristles;
the rotatable base being rotatably mounted into the fluid reservoir;
the base plate of the first brush being removably and axially mounted to the rotatable base;
the base plate of the first brush being positioned in between the fluid reservoir and the reservoir open end;
the base plate of the second brush being removably mounted into the lid;
the lid being removably attached into the fluid reservoir, opposite the rotatable base;
the base plate of the second brush being positioned offset and concentric with the base plate of the first brush;
the plurality of bristles for the first brush and the plurality of bristles for the second brush being oriented towards each other;
the fluid reservoir being in fluid communication with the lid through the base plate of the first brush and through the base plate of the second brush;
a second stem;
the second brush further comprises a plate collar;
the second stem being connected normal to the lid;
the second stem protruding from the lid;
the second stem holding the second brush in place within the lid;
the second stem being positioned centrally to the base plate of the second brush;
the second stem being axially attached to the plate collar of the second brush;
the second brush secured to the lid through the second stem;
a second squeeze lock;
the second stem being axially attached to the plate collar of the second brush by the second squeeze lock;
the second squeeze lock locking the second brush to the second stem, preventing the second brush from separating from the second stem; and
the second squeeze lock retaining the second brush, preventing the second brush from separating from the second stem.

2. The oral appliance cleaner and holder as claimed in claim 1 further comprises:
a first stem;
the fluid reservoir further comprises a reservoir collar;
the first brush further comprises a plate collar;
the first stem being connected normal to the rotatable brush;
the first stem being positioned centrally to the base plate of the first brush;
the first stem being rotatably mounted through the reservoir collar; and
the first stem being axially attached to the plate collar of the first brush.

3. The oral appliance cleaner and holder as claimed in claim 2 further comprises:
a first squeeze lock
an annular receiving cavity
a sealing ring;
the first stem being axially attached to the plate collar of the first brush by the first squeeze lock;
the annular receiving cavity being integrated around the first stem, adjacent to the base plate of the first brush; and
the annular receiving cavity being engaged by the sealing ring.

4. The oral appliance cleaner and holder as claimed in claim 1 further comprises:
the first brush and the second brush each further comprise a plurality of slots;
the plurality of slots being radially distributed about the base plate; and
a plurality of holes traversing through the base plate.

5. The oral appliance cleaner and holder as claimed in claim 1 further comprises:
a male threading;
a female threading;
the male threading being helically connected around the lid, adjacent to the lid open end;
the female threading being helically connected within the fluid reservoir, adjacent to the reservoir open end; and
the male threading being removably engaged to the female threading.

6. The oral appliance cleaner and holder as claimed in claim 1 further comprises:
a base grip;
a reservoir grip;
a lid grip;
the base grip being laterally integrated around the rotatable base;
the reservoir grip being laterally integrated around the fluid reservoir; and
the lid grip being laterally integrated around the lid.

7. An oral appliance cleaner and holder comprises:
a rotatable base;
a fluid reservoir;
a lid;
a first brush;
a second brush;
the fluid reservoir comprises a reservoir open end;
the lid comprises a lid open end;
the first brush and the second brush each comprise a base plate and a plurality of bristles;
the first brush and the second brush each further comprise a plurality of slots;
the rotatable base being rotatably mounted into the fluid reservoir;
the base plate of the first brush being removably and axially mounted to the rotatable base;
the base plate of the first brush being positioned in between the fluid reservoir and the reservoir open end;
the base plate of the second brush being removably mounted into the lid;
the lid being removably attached into the fluid reservoir, opposite the rotatable base;
the base plate of the second brush being positioned offset and concentric with the base plate of the first brush;
the plurality of bristles for the first brush and the plurality of bristles for the second brush being oriented towards each other;
the fluid reservoir being in fluid communication with the lid through the base plate of the first brush and through the base plate of the second brush;
the plurality of slots being radially distributed about the base plate;
a plurality of holes traversing through the base plate;
a second stem;
the second brush further comprises a plate collar;
the second stem being connected normal to the lid;

the second stem protruding from the lid;
the second stem holding the second brush in place within the lid;
the second stem being positioned centrally to the base plate of the second brush;
the second stem being axially attached to the plate collar of the second brush;
the second brush secured to the lid through the second stem;
a second squeeze lock;
the second stem being axially attached to the plate collar of the second brush by the second squeeze lock;
the second squeeze lock locking the second brush to the second stem, preventing the second brush from separating from the second stem; and
the second squeeze lock retaining the second brush, preventing the second brush from separating from the second stem.

8. The oral appliance cleaner and holder as claimed in claim 7 further comprises:
a first stem;
the fluid reservoir further comprises a reservoir collar;
the first brush further comprises a plate collar;
the first stem being connected normal to the rotatable brush;
the first stem being positioned centrally to the base plate of the first brush;
the first stem being rotatably mounted through the reservoir collar; and
the first stem being axially attached to the plate collar of the first brush.

9. The oral appliance cleaner and holder as claimed in claim 8 further comprises:
a first squeeze lock
an annular receiving cavity
a sealing ring;
the first stem being axially attached to the plate collar of the first brush by the first squeeze lock;
the annular receiving cavity being integrated around the first stem, adjacent to the base plate of the first brush; and
the annular receiving cavity being engaged by the sealing ring.

10. The oral appliance cleaner and holder as claimed in claim 7 further comprises:
a male threading;
a female threading;
the male threading being helically connected around the lid, adjacent to the lid open end;
the female threading being helically connected within the fluid reservoir, adjacent to the reservoir open end; and
the male threading being removably engaged to the female threading.

11. The oral appliance cleaner and holder as claimed in claim 7 further comprises:
a base grip;
a reservoir grip;
a lid grip;
the base grip being laterally integrated around the rotatable base;
the reservoir grip being laterally integrated around the fluid reservoir; and
the lid grip being laterally integrated around the lid.

12. An oral appliance cleaner and holder comprises:
a rotatable base;
a fluid reservoir;
a lid;
a first brush;
a second brush;
a base grip;
a reservoir grip;
a lid grip;
the fluid reservoir comprises a reservoir open end;
the lid comprises a lid open end;
the first brush and the second brush each comprise a base plate and a plurality of bristles;
the first brush and the second brush each further comprise a plurality of slots;
the rotatable base being rotatably mounted into the fluid reservoir;
the base plate of the first brush being removably and axially mounted to the rotatable base;
the base plate of the first brush being positioned in between the fluid reservoir and the reservoir open end;
the base plate of the second brush being removably mounted into the lid;
the lid being removably attached into the fluid reservoir, opposite the rotatable base;
the base plate of the second brush being positioned offset and concentric with the base plate of the first brush;
the plurality of bristles for the first brush and the plurality of bristles for the second brush being oriented towards each other;
the fluid reservoir being in fluid communication with the lid through the base plate of the first brush and through the base plate of the second brush;
the plurality of slots being radially distributed about the base plate;
a plurality of holes traversing through the base plate;
the base grip being laterally integrated around the rotatable base;
the reservoir grip being laterally integrated around the fluid reservoir;
the lid grip being laterally integrated around the lid;
a second stem;
a second squeeze lock;
the second brush further comprises a plate collar;
the second stem being connected normal to the lid;
the second stem protruding from the lid;
the second stem holding the second brush in place within the lid;
the second stem being positioned centrally to the base plate of the second brush;
the second stem being axially attached to the plate collar of the second brush;
the second brush secured to the lid through the second stem;
the second stem being axially attached to the plate collar of the second brush by the second squeeze lock;
the second squeeze lock locking the second brush to the second stem, preventing the second brush from separating from the second stem; and
the second squeeze lock retaining the second brush, preventing the second brush from separating from the second stem.

13. The oral appliance and cleaner as claimed in claim 12 further comprises:
a first stem;
a first squeeze lock
an annular receiving cavity
a sealing ring;
the fluid reservoir further comprises a reservoir collar;
the first brush further comprises a plate collar;
the first stem being connected normal to the rotatable brush;

the first stem being positioned centrally to the base plate of the first brush;

the first stem being rotatably mounted through the reservoir collar;

the first stem being axially attached to the plate collar of the first brush;

the first stem being axially attached to the plate collar of the first brush by the first squeeze lock;

the annular receiving cavity being integrated around the first stem, adjacent to the base plate of the first brush; and the annular receiving cavity being engaged by the sealing ring.

14. The oral appliance cleaner and holder as claimed in claim 12 further comprises:

a male threading;

a female threading;

the male threading being helically connected around the lid, adjacent to the lid open end;

the female threading being helically connected within the fluid reservoir, adjacent to the reservoir open end; and the male threading being removably engaged to the female threading.

\* \* \* \* \*